United States Patent [19]

Norman, Jr.

[11] Patent Number: 5,508,262
[45] Date of Patent: Apr. 16, 1996

[54] INTERLEUKIN-1 RECEPTOR ANTAGONIST DECREASES SEVERITY OF ACUTE PANCREATITIS

[75] Inventor: James G. Norman, Jr., Tampa, Fla.

[73] Assignee: University of South Florida, Tampa, Fla.

[21] Appl. No.: 167,698

[22] Filed: Dec. 15, 1993

[51] Int. Cl.$^6$ .............................. A61K 38/00; C07K 7/10
[52] U.S. Cl. .................. 514/8; 514/12; 530/324; 530/351
[58] Field of Search ........................... 514/8, 12; 530/351

[56] References Cited

U.S. PATENT DOCUMENTS

| | | | |
|---|---|---|---|
| 4,439,196 | 3/1984 | Higuchi | 604/892.1 |
| 4,447,224 | 5/1984 | DeCant, Jr. et al. | 604/67 |
| 4,447,233 | 5/1984 | Mayfield | 604/152 |
| 4,475,196 | 10/1984 | LaZor | 371/29.1 |
| 4,486,194 | 12/1984 | Ferrara | 604/308 |
| 4,487,603 | 12/1984 | Harris | 604/152 |
| 4,522,827 | 6/1985 | Marlettini et al. | 514/671 |
| 4,902,708 | 2/1990 | Kim | 514/419 |
| 4,975,464 | 12/1990 | Imaki et al. | 514/423 |
| 5,196,402 | 3/1993 | Braganza et al. | 514/9 |
| 5,220,018 | 6/1993 | Bock et al. | 540/509 |

OTHER PUBLICATIONS

Grewal, et al, Surgery, Feb., 1994, pp. 213–221.
Grewal, et al, Am. J. Surg. 167(1), 214–20, 1994.
Guice, et al J. Surg. Res, 51(6) 495–9. 1991.
Leach et al., 1992, "New Perspectives on Acute Pancreatitis", Scan. J. Gastroenterol 27 Suppl. 192:29–38.
Murayama et al., 1990, "Does Somatostatin Analogue Prevent Exper. Acute Pancreatitis?" Arch. Surg. 125:1570–1572 (Dec.).
Zhu et al., 1991, "Somatostatin analogue is protective against retrograde bile salt–induced pancreatitis in rat", Pancreas 6:609–613.
Spillenaar et al., 1989, "Attempts to reduce post–transplant pancr. in rats and dogs with somatostatin analogue SMS 201–995," Transplant Proceed 21:2829–2830.
Dinarello et al., 1993, "Anticytokine Strategies in Treatment of Systemic Inflammatory Response Syndrome", JAMA 269(14):1829–1834.
Steer, 1992, "How and where does acute pancreatis begin?" Arch. Surg 127:1350–1353.
Tani et al., 1987, "Histologic and biochemical alterations in experimental acute pancreatis induced by supramaximal caerulein stimulation", Int. J. Pancretology. 2:337–348.
Van Ooijen et al., 1990, "Significance of thromboxane $A_2$ and Prostaglandin $I_2$ in acute necrotizing pancreatitis in rats", Digestive Dis. and Sciences, 35:1078–1084.
Schoenberg et al., 1992, "The role of oxygen radicals in experimental acute pancreatitis", Free Radical Biology & Medicine, 12:515–522.
Kelly et al., 1993, "Microvasculature of the pancreas, liver, and kidney in caerulein–induced pancreatitis", Arch Sug, 128:293–295.
Guice et al., 1991, "Anti–tumor Necrosis Factor Antibody Augments Edema Formation in Caerulein–Induced Acute Pancreatitis", 51:495–499.
Heath et al., 1993, "Role of interleukin–6 in mediating the acute phase protein response and potential as an early means of severity assessment in acute pancreatitis", Pancreas 66:45–45.
Larsen and Henson, 1983, "Mediators of Inflammation", Immunol. 1:335–359.
Deitch, 1992, "Multiple Organ Failure", Ann. Surg. 216:117–134.
Michie and Wilmore, 1990, "Sepsis, Signals, and Surgical Sequelae (A Hypothesis)", Arch. Surg. 125:531–536.
Ellison et al., 1981, "Demonstration and Characterization of Hemoconcentrating Effect of Ascitic Fluid That Accumulates . . ." J. Surg. Research 30:241–248.
Wakabayashi et al., 1991, "A specific receptor antagonist for interleukin 1 prevents E. coli–induced shock in rabbits", FASEB J. 5:338–343.
Okusawa et al., 1988, "Interleukin–1 induces a shock–like state in rabbits. Synergism with tumor necrosis factor and the effect of cyclooxygenase inhibition", J. Clin. Invest. 81:1162.
Ohlsson et al., 1990, "Interleukin–1 receptor antagonist reduced mortality from endotoxin shock", Nature 348:550–551.
Aiura et al., 1991, "Interleukn–1 receptor antagonist blocks hypotension in rabbit model of gram–positive septic shock", Cytokine 4:498.
Fischer et al., 1991, "A comparison between effects of interleukin–1α administration and sublethal endotoxemia in primates", Am. J. Physiol. 261:R444.
Waage and Espevik, 1988, "Interleukin–1 potentiates the lethal effect of tumor necrosis factor/cachectin in mice", J. Exp. Med. 1678:1987.
Fischer et al., "Interleukn–1 Receptor Blockade Improves Survival and Hemodynamic Performance in E. coli Septic Shock . . . ", J. Clin. Invest. 89:1551–1557.
Granowitz et al., 1992, "Pharmacokinetics, Safety, Immunomodulatory Effects of Human Recombinant Interluekin–1 Receptor Antagonist in Healthy Humans", Cytokine 4(5):353–360.
Bloedow et al., 1992, "Intravenous Disposition of Interleukin–1 Receptor Antagonist in Healthy Volunteers", Amer. Soc. Clin. Pharm. and Therapeutics, Orlando, Florida (Abstract).
Investigator's Handbook, Cancer Therapy Evaluation Program, National Cancer Institute, pp. 22–23—no date on ref.
Driscoll, 1984, "The Preclinical New Drug Research Program of Nat. Cancer Institute", Cancer Treatment Reports 68:63–76.

(List continued on next page.)

Primary Examiner—Jill Warden
Assistant Examiner—S. G. Marshall
Attorney, Agent, or Firm—Kohn & Associates

[57] ABSTRACT

A method for treating acute pancreatitis comprising administering an effective amount of Interleukin-1 receptor antagonist (IL-1ra) or a pharmaceutically acceptable salt thereof to a person afflicted with that condition.

6 Claims, 2 Drawing Sheets

OTHER PUBLICATIONS

Saluja et al., 1985, "In Vivo rat pancreatic acinar cell function during supramaximal stimulation with caerulein." *Amer. Physiol. Soc.* pp. G702–G710.

Manso et al., 1992, "Cerulein–Induced Acute Pancreatitis in the Rat", *Digestive Diseases and Sciences,* 37:364–368.

Protocol No. 0556, 1993, "Study to Evaluate Safety and Efficacy of Human Recombinant Interleukin–1 Receptor Antagonist (IL–1ra) . . . ", A Randomized, Double–Blind, Placebo–Controlled, Multicenter Trial.

Opal et al., 32nd ICAAC, Oct. 1992, "Phase II Interleukin–1 Receptor Antagonist Sepsis Syndrome Trial: Analysis of Clin., Cytokine and Microbial Features with Outcome" (Abstract).

Fisher et al., Oct. 1991, American College of Chest Physicians, "Interleukin–1 Receptor Antagonist (IL–1ra) Reduced Mortality in Patients with Sepsis Syndrome" (Abstract).

Grewal et al., Feb. 1994, "Induction of tumor necrosis factor in severe acute pancreatitis and its subsequent reduction after hepatic passage", *Surgery* 115(2):213–221.

Grewal et al., Jan. 1994, "Amelioration of Physiologic and Biochemical Changes of Acute Pancreatitis Using an Anti–TNF–α Polyclonal Antibody" *Amer. J. Surg.* 167:214–219.

Dower et al., 26th Annual Scientific Mtg., European Soc. for Clinical Investigation, Apr. 1–4, 1992, Vienna, Austria.

Fisher et al., 1994, "Initial evaluation of human recombinant IL–1 receptor antagonist in treatment of sepsis syndrome . . . ", *Critical Care Medicine* 22(1):12–21.

Gjørup et al., 1992, "Double–Blinded Multicenter Trial of Somatostatin in Treatment of Acute Pancreatitis", *Surgery, Gyn & Ob.* 175:397–.

Fisher et al., 1993, "Study Evaluating Efficacy of Human Recombinant Interleukin–1 Receptor Antanist Treatment of Patients with Sepsis Syndrome . . . " *Clin. Intensive Care* 4:8S.

Dinarello and Wolff, Jan. 1993, "The role of interleukin–1 in disease", *New England J. Med.,* 328(2)106–113.

Innes et al., 1986, "The Vasoactive Properties of Ascitic Fluid in Acute Pancreatitis in Porcine Model", *Arch. Surg.* 121:665 (Jun.).

INTERLEUKIN-1 RECEPTOR ANTAGONIST DECREASES SEVERITY OF ACUTE PANCREATITIS

TECHNICAL FIELD

The present invention relates to a method for treating acute pancreatitis.

BACKGROUND OF THE INVENTION

Acute pancreatitis is a common clinical problem which remains evasive of specific therapy.[1] Each year more than 15,000 admissions to U.S. hospitals are caused by acute pancreatitis. It is most often caused by alcoholism or biliary tract disease. Less commonly, it is associated with hyperlipemia, hyperparathyroidism, abdominal trauma, vasculitis or uremia. The average length of hospitalization for the disease is 12.4 days, with a significant number of patients staying much longer because of associated complications.

There are no medical therapies or pharmacologic agents currently available which have been shown to decrease the severity, duration, complication rate, or mortality for this common disease. Over the past decade, a somatostatin analog has undergone several clinical, as well as laboratory trials, in an attempt to show beneficial effects of suppressing pancreatic exocrine function pharmacologically during acute pancreatitis. The majority of investigators have shown beneficial effects only with treatment prior to the onset of pancreatitis, and disappointing results when somatostatin was given after the acute inflammatory process had started.[2,3,4]

With more recent understanding of the complex mechanisms of tissue and cellular injury associated with inflammatory processes, such as sepsis,[5] it is reasonable to assume that many of these inflammatory processes are not specific to sepsis syndromes alone. Several authors have suggested that much of the intrinsic pancreatic damage seen in acute pancreatitis is due to the release of toxic substances from macrophages and other white blood cells which migrate into the damaged gland.[6,7,8,9,10,11,12] These substances are known as cytokines and are now well known as mediators of inflammation and tissue injury.

A curious aspect of acute pancreatitis is the systemic response which is seen following inflammation initiated within the pancreas. Acute pulmonary, renal, and hepatic failure, generalized water retention, hypocalcemia, hypoxia, and acid/base disturbances are all possible complications of pancreatitis. The mechanism for complications of pancreatitis. The mechanism for the involvement of these other organ systems is unclear, but probably involves activation of the cytokine cascade, including interleukin-1 (IL-1), interleukin-6 (IL-6), and tumor necrosis factor (TNF) in a manner not significantly different from sepsis syndromes.[12,13,14,15] Serum levels of these peptides have been shown to correlate to a high degree with the severity of acute pancreatitis in humans, and can also be demonstrated within pancreatic ascites.[12,16]

The administration of IL-1 to rabbits[17,18,19,20] and primates[21] has been shown to result in hypotension, tachycardia, lung edema, renal failure, and, eventually, death, depending on the dose. These signs and symptoms are similar to those demonstrated by patients with severe acute pancreatitis. When the serum from the IL-1 treated animals is examined, the elevation of other cytokines is evident, mimicking the levels seen in acute pancreatitis in humans.[11,12] There is a large body of evidence currently available which supports the role of IL-1 as a major mediator of the systemic response to diseases such as sepsis and pancreatitis and as an activator of the remaining members of the cytokine cascade.[5] Fischer et al.[21] demonstrated that the administration of a naturally occurring antagonist to IL-1 will significantly blunt the cytokine cascade and improve survival in baboons given a lethal dose of live bacteria. In this study, IL-1 receptor antagonist (IL-1ra) significantly attenuated the decrease in mean arterial pressure and cardiac output and improved survival over control. The systemic IL-1 and IL-6 responses observed as a result of the bacteremia were diminished significantly, correlating with a decrease in the systemic response to the sepsis.

Studies by Aiura et al.[20] have shown that IL-1ra is protective in a rabbit model of hypotensive gram-positive septic shock. The administration of IL-1ra in this animal model has been shown to maintain mean arterial pressure compared to control, as well as decreasing lung water and maintaining urine output. This work demonstrated the role of IL-1 and the protective role of IL-1ra in gram-positive shock which was thought to be due to a separate mechanism from gram-negative shock. The common pathway for the systemic manifestations of these two different models of shock has been shown to involve IL-1 as a central mediator. Evidence is mounting for the role of IL-1 as the principal mediator in a patient's clinical response to multiple different stresses regardless of the etiology (including acute pancreatitis).

U.S. Pat. Nos. 4,522,827 and 4,902,708 disclose methods of treating acute pancreatitis. However, none of these patents take into effect the specific pathology of the disease, thereby proposing treatments which are not specific and are directed to the symptoms only, not the underlying mechanism.

U.S. Pat. No. 5,196,402 discloses the use of S-adenosyl methionine for the use of treatment of pancreatitis in the context of a complication in the graft rejection inpancreas transplant, a very uncommon procedure. The patent does not address acute pancreatitis as a disease in the nontransplant patient. The vast majority of cases of pancreatitis are not associated with pancreatic transplants.

Treatments are needed which take into account that the local, as well as systemic, effects seen during acute pancreatitis are due to activation of the cytokine cascade whereby proximal inhibition of this cascade will decrease the severity of the inflammatory process.

SUMMARY OF THE INVENTION AND ADVANTAGES

According to the present invention, a method for treating acute pancreatitis is provided. The method comprises administering to a person afflicted with that condition an effective amount of Interleukin-1 receptor antagonist (IL-1ra) or a pharmaceutically acceptable salt thereof.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
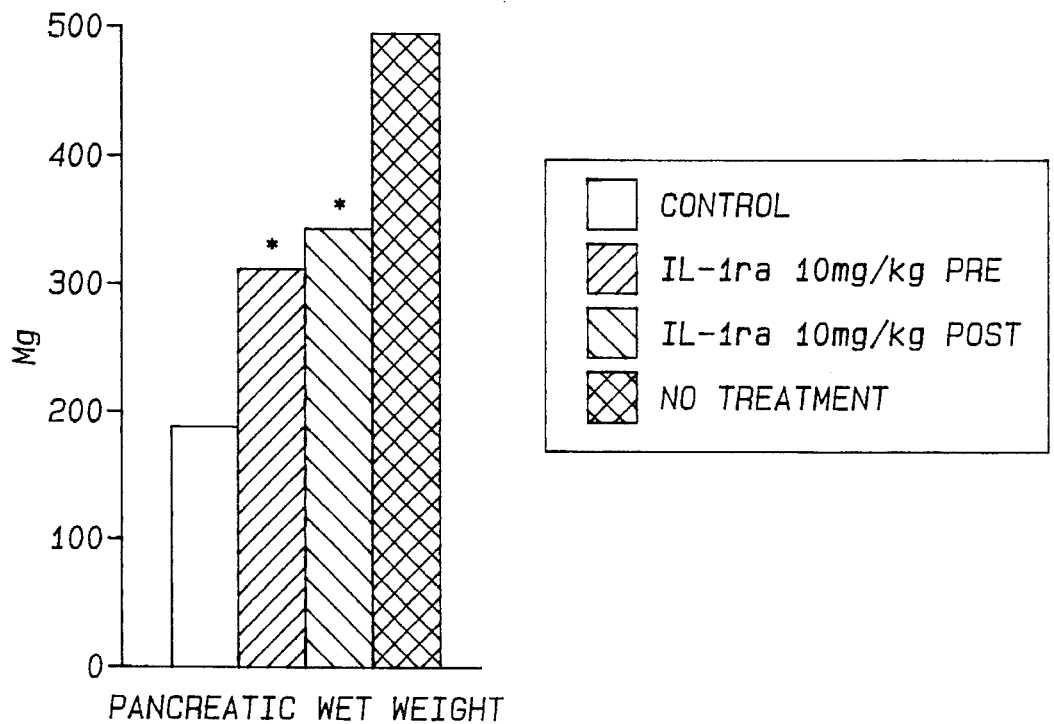
FIG. 1 is a graph showing the pancreatic wet weight in controls (shaded), IL-1ra 10 mg/kg pretreatment (solid), IL-1ra 10 mg/kg post-treatment (diagonal), and untreated disease control (cross-hatching) with * indicating p<0.01 compared to no treatment.
Figure 2:
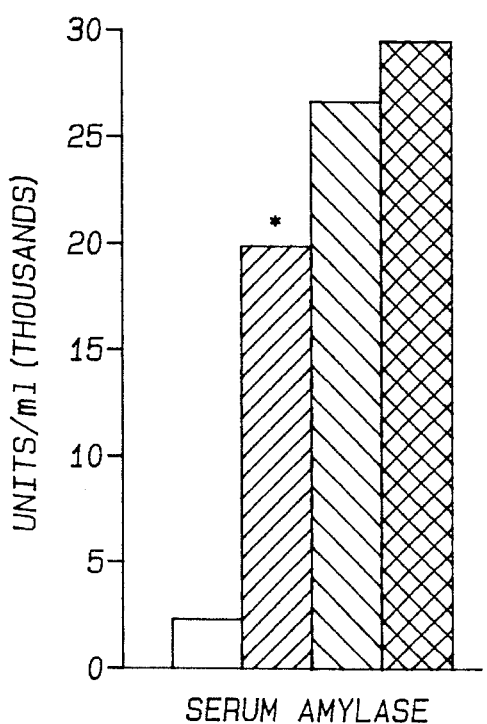
FIG. 2 is a graph showing the serum amylass levels in groups as in FIG. 1 with * indicating p<0.05 compared to no treatment.
Figure 3:
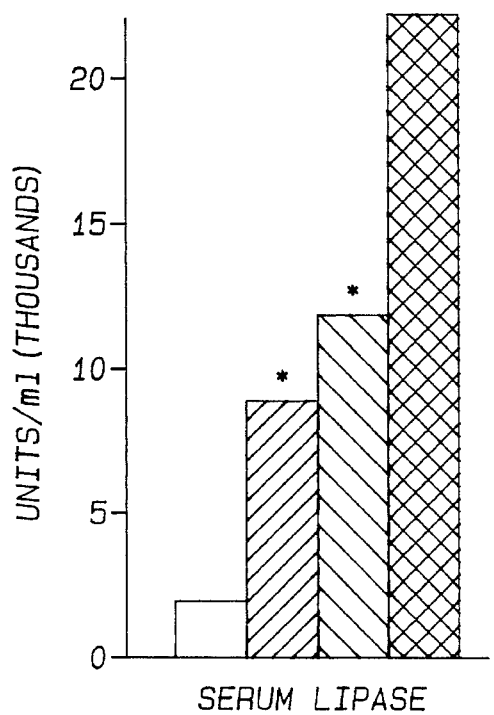
FIG. 3 is a graph showing the serum lipass levels in groups as in FIG. 1 with * indicating p<0.0001 compared to no treatment.
Figure 4:
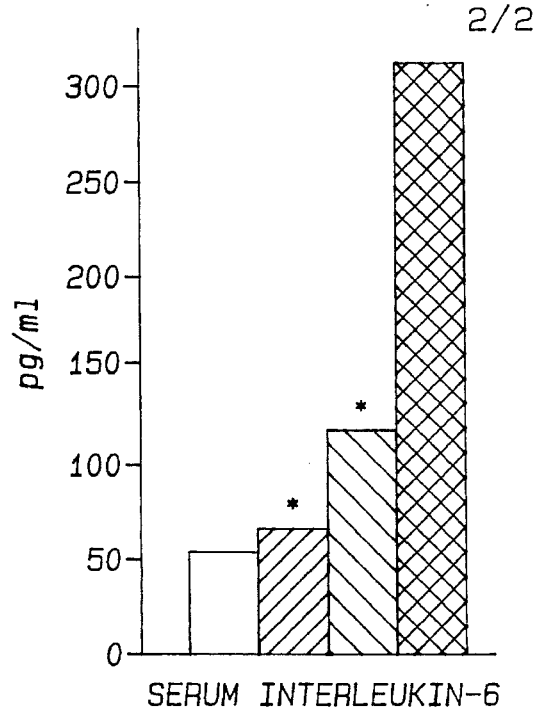
FIG. 4 is a graph showing the serum interleukin-6 levels in groups as in FIG. 1 with * indicating p<0.0001 compared to no treatment.

IL-1ra is a naturally occurring peptide secreted by macrophages in response to many of the same stimuli which cause the secretion of IL-1 itself. IL-1ra is the only known naturally occurring antagonist to the cytokines and recognizes receptors on various cell types and blocks IL-1 mediated responses by occupying the receptor.[17,18,19,20,21] In humans, IL-1ra is a naturally occurring group of molecules; three forms have been characterized (two glycosylated and one non-glycosylated).

According to the present invention, a method for treating acute pancreatitis is provided. The method comprises administering to a person afflicted with that condition is administered an effective amount of Interleukin-1 receptor antagonist (IL-1ra) or a pharmaceutically acceptable salt thereof.

The safety of IL-1ra after intravenous administration has been demonstrated during the past three years in mice, rats, rabbits, dogs, primates, and humans.[17,19,20,21,22,23,24] In normal volunteers, IL-1ra has been demonstrated to have a half-life of approximately two hours after intravenous administration and the plasma clearance of IL-1ra appeared to correlate with creatine clearance.[25] Hence, there already exists a regimen for IL-1ra administration for humans.

The IL-1ra to be used can be administered in combination with other drugs or singly consistent with good medical practice. The other drugs can be somatostatin or an analog (i.e., Sandostatin®) and prostaglandin inhibitors (i.e., non-steroidal, anti-inflammatory drugs such as aspirin, indomethacin, ibuprofen, etc.). Additionally, steroids or other drugs designed to suppress the immune system and other synthetic or recombinant antagonists or blockers to cytokines (e.g., soluble TNF receptors, soluble IL-1 receptors, soluble IL-6 receptors or others; monoclonal antibodies to IL-1, IL-6, TNF or others, etc.) can be administered. Further, nitric oxide inhibitors or antagonists, free radical scavengers or anti-oxidants, antagonists or blockers of complement, ecosinoids or their antagonists and antibiotics, as appropriate, can also be administered.

The IL-1ra is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

In the method of the present invention, the IL-1ra can be administered in various ways. It should be noted that the IL-1ra can be administered as the compound or as pharmaceutically acceptable salt and can be administered alone or in combination with pharmaceutically acceptable carriers. The compounds can be administered orally or parenterally including intravenous, intraperitoneally, intranasal and subcutaneous administration. Implants of the compounds are also useful. The patient being treated is a warm-blooded animal and, in particular, mammals including man.

When administering the IL-1ra parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the IL-1ra can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

These patents are incorporated herein by reference. Many other such implants, delivery systems, and modules are well known to those skilled in the art.

A pharmacological formulation of the IL-1ra utilized in the present invention can be administered orally to the patient. Conventional methods such as administering the compounds in tablets, suspensions, solutions, emulsions, capsules, powders, syrups and the like are usable. Known techniques which deliver the IL-1ra orally or intravenously and retain the biological activity are preferred.

In one embodiment, the IL-1ra can be administered initially by intravenous injection to bring blood levels of IL-1ra to a suitable level. The patient,s IL-1ra levels are then maintained by an oral dosage form, although other forms of administration, dependent upon the patient,s condition and as indicated above, can be used. The quantity of IL-1ra to be administered will vary for the patient being treated and will vary from about 100 ng/kg of body weight to 100 mg/kg of body weight per day and preferably will be from 10 µg/kg to 10 mg/kg per day.

In one preferred embodiment, if the patient is diagnosed with severe acute pancreatitis, then the patient will be aggressively treated for 72 hours and will receive intravenously a loading dose of 100 mg in a total volume of 10 ml followed by a 72-hour continuous infusion. The continuous infusion will consist of 2.0 mg/kg/hr. The infusion will be done by preparing 100 ml of the drug in saline for each 12-hour period. It will be infused by utilizing a volumetric infusion pump at a rate of 8.3 ml/hr. Any residual IL-1ra at the end of the 12 hours will be infused before the subsequent 12-hour infusion is initiated. At the completion of the 72-hour infusion, the patient is evaluated and, based on the patient,s condition, infusion will be continued, administration switched to oral dosage, or the drug discontinued.

The practice and utility of the present invention is shown in the following example:

MATERIALS AND METHODS

The specification and claims provide guidance for the use of the invention in humans. The *Investigator's Handbook*[26] provided by the National Cancer Institute (page 23) indicates that the starting dose for Phase I trials is based on the mouse equivalent $LD_{10}$. Further, the manual (page 22) indicates that animal studies carried out prior to Phase I trials provide the investigator with a prediction of the likely effects.[27] Therefore, the presented rodent model data is not only acceptable in determining human doses and protocols, but is considered highly predictive.

Acute edematous, necrotizing pancreatitis was induced in adult male Swiss mice weighing more than 35 grams using caerulein—an analog of cholecystokinin. Mice were divided into four groups with three of the groups receiving caerulein 50 µg/kg by intraperitoneal (IP) injection in four doses over three hours as previously described.[2,7,9,12,28,29]

Group 1 was a control group (n–9) which received only IP saline injections. Group 2 (n=12) was an untreated disease control. Group 3 (n=12) received three injections (10 mg/kg/hr) starting one hour prior to induction of pancreatitis. Group 4 (n=12) received three injections (10 mg/kg/hr) starting one hour after induction of pancreatitis.

The IL-1ra used in this study is produced in *E. coli* by Synergen Corporation (Boulder, Col.) by utilizing recombinant DNA technology and is identical to the non-glycosylated human form of human IL-1ra except for the addition of one terminal methionine amino acid.

After nine hours, all animals were euthanized, the blood collected, and the pancreata surgically excised and weighed. Serum was assayed for amylase, lipase, IL-6, and TNF levels. Each pancreas was fixed, stained, and graded histologically in a blinded fashion for interstitial edema, granulocyte infiltration, acinar vacuolization, and acinar cell necrosis as described previously.[7,27,28] Additionally, serum levels of IL-1ra were determined, therefore allowing comparisons between dosage, serum level, systemic cytokine response, and degree of pancreatic damage.

IL-6, IL-1, IL-1ra, and TNF were measured by commercially available ELISA kits (Genzyme Corp., Boston, Mass.). All specimens were run in triplicate. Serum levels of amylase and lipase were measured on a Kodak Ectachem 700 automated analyzer (Eastman Kodak Company, Rochester, N.Y.).

Histologic slides were prepared as is known in the art after rapid excision and subsequent fixation in 10% formalin. The tissues were paraffin embedded as is known in the art and then stained with Hematoxylin and Eosin in a standard fashion. These slides were examined and graded in a blinded fashion by a board certified pathologist.

Results

Figure 5:
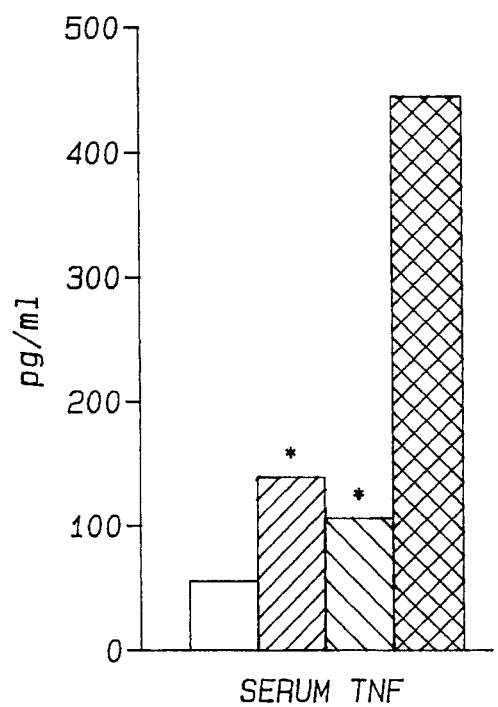
FIG. 5 is a graph showing the serum TNF levels in groups as in FIG. 1 with * indicating P<0.0001 compared to no treatment.

In these experiments, acute pancreatitis was induced in 45 mice using caerulein. Acute edematous, necrotizing pancreatitis is present within an hour of caerulein injection and reaches a peak effect approximately nine hours later. By treating mice with IL-1ra prior to or after the induction of pancreatitis, applicants were able to show a significant decrease in pancreatic wet weight ($p<0.01$), serum amylase ($p<0.05$), lipase ($p<0.0001$), and IL-6 ($p<0.0001$) as shown in FIGS. 1–4 and Table I, respectively. TNF ($p<0.0001$) was also significantly reduced (FIG. 5). All statistics noted are significant by two-tailed Wilcoxon test. Additionally, there was a decrease in the number of polymorphonuclear white blood cells (PMNs) within the capillaries of the lungs and pancreas. Histologic studies of these pancreata were performed in a blinded fashion and showed a significant decrease ($p<0.05$) in total organ edema, acinar necrosis, acinar vacuolization, and inflammation in those animals treated with IL-1ra. An important finding in these experiments was that treatment with IL-1ra within two hours after the onset of pancreatitis was nearly as protective as pretreatment.

These series of experiments were repeated using both higher and lower does of IL-1Ra. In one experiment, all animals received IL-1ra at a dose of 100 mg/kg/hrX3. All the previous findings were confirmed, but no significant benefit could be found with the higher dose. When the dose of IL-1ra was decreased to 1 mg/kg/hrx3, the benefits were seen in all categories except amylase levels. This dose, however, did not show quite as much decrease in wet weight or the levels of IL-6 and TNF as did the 10 mg/kg/hrx3 dose. These dose response experiments confirm the efficacy of IL-1ra in the treatment of pancreatitis when proper levels of the drug are maintained.

The example provides guidance for the use of the invention in humans. The *Investigator's Handbook*[26] provided by the National Cancer Institute (page 23) indicates that the starting dose for Phase I trials is based on the mouse equivalent $LD_{10}$. In fact, Phase I trials of IL-1ra have been completed.[24] Further, the manual (page 22) indicates that animal studies carried out prior to Phase I trials provide the investigator with a prediction of the likely effects.[12] Therefore, the presented rodent model data is not only acceptable in determining human doses and protocols but is considered highly predictive. Based on the available data from the Phase I trials and Phase II trials in the treatment of sepsis[30] combined with the present invention allows the treatment of pancreatitis in humans.

Further, the cytokine activation in fulminant pancreatitis is similar to that of sepsis. The blockade of the cascade applicants have shown is similar to that shown in animal and human studies using IL-1ra for sepsis. A better understanding of the role played by specific cytokines in this systemic reaction has provided insight into effective therapies for severe pancreatitis, in particular the therapeutic use of IL-1ra in acute pancreatitis.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

| GROUP | WET WT (mg) | AMYLASE (SU) | LIPASE (IU) | IL-6 (ng/kg) | TNF (ng/kg) |
| --- | --- | --- | --- | --- | --- |
| 1 | 188 ± 0.1 | 2204 ± 156 | 715 ± 58 | 54 ± 5 | 63 ± 9 |
| 2 | 493 ± .04* | 29465 ± 1756* | 22259 ± 3155* | 315 ± 51* | 442 ± 30* |
| 3A | 320 ± .02** | 21480 ± 2393** | 8976 ± 1685** | 65 ± 11** | 136 ± 3** |
| 4A | 341 ± .04** | 28088 ± 4494** | 11916 ± 2648** | 118 ± 17** | 101 ± 10** |

Results are expressed as mean ± SEM, significance accepted if $p < 0.05$ by two-tailed Wilcoxon test.
*compared to control (Group 1)
**compared to untreated pancreatitis (Group 2)

REFERENCES

1. Leach SD, Gorelick S, Modlin IM, New Perspectives on Acute Pancreatitis. Scan. J Gastroenterol 1992:27 Suppl 192:29–38.
2. Murayama KM, Drew JB, and Joehl RJ: Does somatostatin analogue prevent experimental acute pancreatitis? Arch Surg 1990;125:1570–1572.
3. Zhu ZH, Holt s, El-Lbishi MS, Grady T, Taylor, TV, and Powers RE:A somatostatin analogue is protective against retrograde bile salt-induced pancreatitis in the rat. Pancreas 1991;6:609–613.
4. Spillenaar Bilgen EJ, Marquet RL, Baumgartner D, de Bruin RWF, Lamberts SWJ, and Jeekel J: Attempts to reduce post-transplant pancreatitis in rats and dogs with the somatostatin analogue SMS 201–995. Transplant Proceed 1989;21:2829–2830.
5. Dinarello CA, Gelfand JA, Wolf SM, Anticytokine Strategies in Treatment of Systemic Inflammatory Response Syndrome. JAMA, 4/1993;269:1829–1834.
6. Steer ML: How and where does acute pancreatitis begin? Arch Surg 1992;127:1350–1353.
7. Tani S, Otsuki M, Itoh H, Fujii M, Nakamura T, Oka T, and Baba S: Histologic and biochemical alterations in experimental acute pancreatitis induced by supramaximal caerulein stimulation. International J Pancreatology 1987;2:337–348.
8. Van Ooijen B, Kort WJ, Tinga CJ, and Wilson JHP: Significance of thromboxane $A_2$ and Prostaglandin $I_2$ in acute necrotizing pancreatitis in rats. Digestive Disease and Sciences 1990;35:1078–1084.
9. Schoenberg MH, Büchler, and Berger HG: The role of oxygen radicals in experimental acute pancreatitis. Free Radical Biology & Medicine 1992;12:515–522.
10. Kelly DM, McEntree GP, McGeeney KF, and Fitzpatrick JM: Microvasculature of the pancreas, liver, and kidney in caerulein-induced pancreatitis. Arch Sug 1993;128:293–295.
11. Guice KS, Oldham KT, Remick DG, Kunkel SL, and Ward PA: Anti-tumor necrosis factor antibody augments edema formation in caerulein-induced pancreatitis. J Surg Res 1991;51:495–499.
12. Heath, D.I., Cruickshank A., Gudgeon M, Jehanli A, Shenkin A, and Imrie CW: Role of interleukin-6 in mediating the acute phase protein response and potential as an early means of severity assessment in acute pancreatitis. Pancreas 1993;66:41–45.
13. Larsen GL, and Henson PM: Mediators of Inflammation. Immunol 1983;1:335–359.
14. Deitch EA: Multiple organ failure. Ann Surg 1992;216:117–134.
15. Michie HR, and Wilmore DW: Sepsis, signals, and surgical sequelae. Arch Surg 1990;125:531–536.
16. Ellison EC, Pappas TN, Johnson JA, Fabri PJ, and Carey, LC: Demonstration and characterization of the hemoconcentrating effect of ascitic fluid that accumulates during hemorrhagic pancreatitis. J Surg Research 1981;30:241–248.
17. Wakabayashi G, Gelfand JA, Burke JF, Thompson RC, and Dinarello CA: A specific receptor antagonist for interleukin-1 prevents E. coli induced shock in rabbits. FASEB J 1991;5:338.
18. Okusawa S, Gelfand JA, Ikejima T, Connolly RJ, and Dinarello CA: Interleukin-1 induces a shock-like state in rabbits. Synergism with tumor necrosis factor and the effect of cyclooxygenase inhibition. J Clin Invest 1988;81:1162.
19. Ohlsson K, Bjork P, Bergenfeldt M, Hageman R and Thompson RC. An interleukin-1 receptor antagonist reduces mortality from endotoxin shock. Nature 1990;348:550.
20. Aiura K, Gelfand JA, Wakabayashi G, Callahan MV, Burke JF, et al: Interleukin-1 receptor antagonist blocks hypotension in a rabbit model of gram-positive septic shock. Cytokine 1991;4:498.
21. Fischer E, Marano MA, Barber A, Hudson AA, Lee K, et al: A comparison between the effects of interleukin-1σ administration and sublethal endotoxemia in primates. Am J Physiol 1991;261:R442.
22. Waage A and Espevik T: Interleukin-1 potentiates the lethal effect of tumor necrosis factor/cachectin in mice. J Exp Med 1988;167:1987.

23. Fischer E, Marano MA, Van Zee KJ, Rock CS, Hawe AS, et al: Interleukin-1 receptor blockade improves survival and hemodynamic performance in Escherichia coli septic shock, but never fails to alter host responses to sublethal endotoxemia. J Clin Invest 1992;89:1551.
24. Granowitz EV, Porat R, Mier JW, Pribble JP. Stiles DM, et al: Pharmacokinetics, safety and immunomodulatory effects of human recombinant interleukin-1 receptor antagonist in healthy humans. Cytokine 1992;4:353.
25. Bloedos DC, Stiles DM, Beshore AL, Granowitz EV, Dinarello, CA, et al. Intravenous disposition of interleukin-1 receptor antagonist in healthy volunteers. Amer. Soc. Clin. Pharmacology and THerapeutics March, 1992. Orlando, FL. (Abstract)
26. *Investigator's Handbook,* Cancer Therapy Evaluation Program, Division of Cancer Treatment, National Cancer Institute, pp. 22–23.
27. Driscoll, J. S, The Preclinical New Drug Research Program of the National Cancer Institute (1984) Cancer Treatment Reports 68:63–76.
28. Saluja A, Saito I, Saluja M, Houlihan MJ, Powers RE, Meldolesi J, and Steer ML: In vivo rat pancreatic acinar cell function during supramaximal stimulation with caerulein. Amer Physiological Society 1985: G702–G710.
29. Manso MA, San Roman JI, de Dios I, Garcia LJ, and Lopez MA: Caerulein-induced acute pancreatitis in the rat. Digestive Disease and Sciences 1992;37:364–368.
30. Protocol No. 0556, A Study to Evaluate the Safety and Efficacy of Human Recombinant Interleukin-1 Receptor Antagonist (IL-1ra) in Increasing Survival in Patients with Severe Sepsis, A Randomized, Double-Blind, Placebo-Controlled, Multicenter Trial (1993).

What is claimed is:

1. A method for treating acute pancreatitis which comprises administering to a person afflicted with acute pancreatitis an effective amount of Interleukin-1 receptor antagonist (IL-1ra) or a pharmaceutically acceptable salt thereof wherein the effective amount of IL-1ra administered is from 100 ng/kg body weight to 100 mg/kg body weight of the patient per day.

2. The method of claim 1 wherein the IL-1ra is suspended in an acceptable carrier.

3. The method of claim 1 wherein the effective amount of IL-1ra is administered initially by an intravenous injection to bring blood levels of IL-1ra to a suitable level after which the patients IL-1ra levels are maintained for as long as clinically indicated.

4. The method of claim 3 wherein the IL-1ra is administered (a) intravenously as a loading dose of 100 mg in a total volume of 10 ml followed by (b) a 72 hour continuous infusion.

5. The method of claim 4 wherein the 72 hour continuous infusion consists of 2.0 mg/kg/hr.

6. The method of claim 1 further comprising administering additional drugs in combination with IL-1ra selected from the group consisting of somatostatins, prostaglandin inhibitors, immunosuppressive drugs, cytokine agonists, cytokine blockers, nitric oxide inhibitors or antagonists, free radical scavengers or anti-oxidants, antagonists or blockers of complement, ecosinoids or their antagonists and antibiotics.

* * * * *